United States Patent
Kaufman

(10) Patent No.: US 8,983,166 B2
(45) Date of Patent: Mar. 17, 2015

(54) METHOD FOR AUTOMATICALLY SEEDING PREVIOUSLY-CLASSIFIED IMAGES AMONG IMAGES OF OBJECTS OF INTEREST FROM A SPECIMEN

(75) Inventor: Howard B. Kaufman, Newton, MA (US)

(73) Assignee: Hologic, Inc., Marlborough, MA (US)

( * ) Notice: Subject to any disclaimer, the term of this patent is extended or adjusted under 35 U.S.C. 154(b) by 316 days.

(21) Appl. No.: 13/427,251

(22) Filed: Mar. 22, 2012

(65) Prior Publication Data

US 2012/0243755 A1 Sep. 27, 2012

Related U.S. Application Data

(60) Provisional application No. 61/466,856, filed on Mar. 23, 2011.

(51) Int. Cl.
| | | |
|---|---|---|
| *G06K 9/00* | (2006.01) | |
| *G06K 9/62* | (2006.01) | |
| *G06F 19/00* | (2011.01) | |
| *G06K 9/03* | (2006.01) | |

(52) U.S. Cl.
CPC ............ *G06F 19/321* (2013.01); *G06F 19/327* (2013.01); *G06F 19/345* (2013.01); *G06F 19/366* (2013.01); *G06K 9/6263* (2013.01); *G06K 9/00127* (2013.01); *G06K 9/033* (2013.01)
USPC ............................. 382/133; 382/128; 382/224

(58) Field of Classification Search
None
See application file for complete search history.

(56) References Cited

U.S. PATENT DOCUMENTS

| | | | | |
|---|---|---|---|---|
| 6,125,194 A | * | 9/2000 | Yeh et al. .................. | 382/132 |
| 7,505,614 B1 | * | 3/2009 | De La Torre-Bueno ...... | 382/128 |
| 7,870,284 B2 | * | 1/2011 | Hunt et al. ................. | 709/232 |
| 8,326,014 B2 | * | 12/2012 | Wong et al. ................ | 382/133 |
| 2004/0253616 A1 | | 12/2004 | Wong et al. | |
| 2010/0174994 A1 | * | 7/2010 | Marx ........................ | 715/738 |

FOREIGN PATENT DOCUMENTS

| | | |
|---|---|---|
| EP | 1 262 900 | 12/2002 |
| WO | 2009/086427 | 7/2009 |

OTHER PUBLICATIONS

PCT International Search Report and Written Opinion for International Application No. PCT/US2012/030116, Applicant Hologic, Inc., forms PCT/ISA/210, 220, and 237, dated Jun. 27, 2012 (22 pages).

Jeremy M. Wolfe, et al., "Low Target prevalence is a stubborn source of errors in visual search tasks", Journal of Experimental Psychology, 2007, vol. 136 No. 4, pp. 623-638.

(Continued)

*Primary Examiner* — Anand Bhatnagar
*Assistant Examiner* — Soo Park
(74) *Attorney, Agent, or Firm* — Vista IP Law Group LLP

(57) ABSTRACT

A computer-assisted method of classifying cytological samples, includes using a processor to analyze images of cytological samples and identify cytological objects of interest within the sample images, wherein the processor (i) displays images of identified cytological objects of interest from the sample images to a reviewer, (ii) accesses a database of images of previously classified cytological objects, and (iii) displays to the reviewer, interspersed with the displayed images of the identified objects of interest from the sample images, one or more images obtained from the database of images of previously-classified objects.

4 Claims, 6 Drawing Sheets

(56) References Cited

OTHER PUBLICATIONS

Jeremy Wolfe, et al., "Target Prevalence Influences Cytologists' Error Rates", Poster Presentations, Cancer Cytopathology, Oct. 25, 2010 (1 page).
Joanne Clarke, et al., "Assuring the quality of quality assurance", Cancer Cytopathology, Jul. 10, 2008 (6 pages).
Karla K. Evans, et al., "Prevalence of Abnormalities Influences Cytologists' Error Rates in Screening for Cervical Cancer", Arch Pathol Lab Med, vol. 135, Dec. 2011 (4 pages).
Victoria Cutler, et al., "Use of threat image projection (TIP) to enhance security performance", QinetiQ Ltd., Oct. 5, 2009 (6 pages).
Andrew Evereed, "If it's not seen often, it's often not seen", 49th Annual Scientific Meeting of the British Society for Clinical Cytology, Sep. 14, 2009 (2 pages).

* cited by examiner

METHOD FOR AUTOMATICALLY SEEDING PREVIOUSLY-CLASSIFIED IMAGES AMONG IMAGES OF OBJECTS OF INTEREST FROM A SPECIMEN

RELATED APPLICATION DATA

The present application claims the benefit under 35 U.S.C. §119 to U.S. provisional patent application Ser. No. 61/466,856, filed Mar. 23, 2011. The foregoing application is hereby incorporated by reference into the present application in its entirety.

FIELD OF THE INVENTION

The present invention is related to systems and methods for characterizing or classifying biological specimens.

BACKGROUND OF THE INVENTION

In the medical industry, there is often a need for a laboratory technician, e.g., a cytotechnologist, to review a cytological specimen for the presence of specified cell types. For example, there is presently a need to review a cervical-vaginal Papanicolaou (Pap) smear slides. Pap smears have been a powerful tool for detecting cancerous and precancerous cervical lesions.

The Pap smear has been credited with reducing mortality from cervical cancer by as much as 70%. This once precipitous drop in the death rate has slowed however, and the mortality rate in the United States for this preventable disease has remained virtually constant, at about 5,000 per year since the mid-eighties. Therefore, about one-third of the 15,000 women diagnosed with cervical cancer annually still die, because the cancer was detected too late.

The prevalence of high grade cervical disease has been decreasing where effective screening programs have been implemented. The prevalence is expected to decrease even further with the adoption of new HPV vaccines. With this decrease in prevalence, there has been an increase in the difficulty of maintaining, monitoring, and measuring cytotechnologist diligence during cytological slide examinations. For example, accurately measuring the sensitivity of an individual screener is difficult when the number of abnormal cases is very low. Also, research of visual search tasks has shown that examiner vigilance and alertness decrease with low target prevalence (e.g., low numbers of abnormal cases).

One technique that has been used to counter quality control difficulties caused by low prevalence of abnormal cases is the seeding of known abnormal slides into the rapid screening workflow of reviewers examining Pap smear slides. Though this technique was implemented in a high volume clinical lab over an extended period of time, the technique required a tedious process of selecting abnormal slides, disguising seeded slides to avoid their identification as seeded slides, and excessive slide handling. A more practical and simpler method for seeding abnormal cases into the workflow of cytological examination is needed.

SUMMARY

One embodiment is directed to a computer-assisted method of classifying cytological samples. The method includes using one or more processors to analyze images of cytological samples and identify cytological objects of interest within the sample images, wherein the one or more processors display images of identified cytological objects of interest from the sample images to a reviewer. Displaying images of the identified objects of interest from the sample images to a reviewer may include displaying images of fields of view of respective cytological samples, each field of view image having one or more identified objects of interest therein.

In this embodiment, the one or more processors also access a database of images of previously classified cytological objects, and display to the reviewer, interspersed with the displayed images of the identified objects of interest from the sample images, one or more images obtained from the database of images of previously-classified objects. A number of images of previously classified objects obtained from the database and displayed to the reviewer may be based upon a threshold rate at which cytological objects of a specified classification (e.g., abnormal cytological objects) are to be displayed to the reviewer. The threshold rate may be a minimum number of images of cytological objects of the specified classification that are displayed to the reviewer, or to a group of reviewers, within a specified amount of time, or within a specified number of cytological sample images.

The one or more processors may further receive input from the reviewer representing a reviewer classification of respective objects shown in the displayed images of previously classified objects, and determine a percentage of said reviewer classifications that match respective previously-determined classifications of said previously classified objects.

Another embodiment directed to a computer-assisted method of classifying cytological samples includes using one or more processors to analyze images of cytological samples and identify cytological objects of interest within the sample images, wherein the one or more processors display images of identified cytological objects of interest from the sample images to a reviewer. Displaying images of the identified cytological objects of interest from the sample images to a reviewer may include displaying images of fields of view of respective cytological samples, each field of view image having one or more identified objects of interest therein.

In this embodiment, the one or more processors also determine a threshold rate at which images of cytological objects of a specified classification (e.g., images of abnormal cytological objects) are displayed to the reviewer. The threshold rate may be a minimum number of images of cytological objects of the specified classification that are displayed to the reviewer, or to a group of reviewers, within a specified amount of time, or within a specified number of cytological sample images.

In this embodiment, the one or more processors also access a database of images of previously classified cytological objects, and display to the reviewer, interspersed with the displayed images of the identified objects of interest from the sample images, one or more images obtained from the database of images of previously classified objects, wherein a number of images of previously classified objects selected from the database and displayed to the reviewer is based on the threshold rate. The one or more processors may further receive input from the reviewer representing a reviewer classification of respective objects shown in the displayed images of previously classified objects, and determine a percentage of said reviewer classifications that match respective previously determined classifications of said previously classified objects.

Yet another embodiment directed to a computer-assisted method of classifying cytological samples includes using one or more processors to analyze images of cytological samples and identify cytological objects of interest within the sample images, wherein the one or more processors display images of identified cytological objects of interest from the sample images to a reviewer, access a database of images of previously classified cytological objects, and display to the reviewer, interspersed with the displayed images of the identified objects of interest from the sample images, one or more images obtained from the database of images of previously classified objects, wherein a number of images of previously classified objects selected from the database and displayed to the reviewer is based on a percentage of the displayed images of previously classified objects that are properly classified by the reviewer. The one or more processors may determine the percentage by receiving input from the reviewer representing a reviewer classification of respective objects shown in the displayed images of previously classified objects, and comparing said reviewer classifications to the respective previously-determined classifications of said previously-classified objects.

Still another embodiment directed to a computer-assisted method of classifying cytological samples includes using one or more processors to analyze images of cytological samples and identify cytological objects of interest within the sample images, wherein the one or more processors display images of identified cytological objects of interest from the sample images to a reviewer, access a database of images of previously-classified cytological objects, each of the objects in the database images having a previously determined classification, wherein the one or more processors, without being prompted by the reviewer, automatically select and display to the reviewer one or more images from the database interspersed with the displayed images of the identified objects of interest from the samples. A number of images of previously classified objects obtained from the database and displayed to the reviewer may be based upon a threshold rate at which cytological objects of a specified classification (e.g., abnormal cytological objects) are to be displayed to the reviewer. For example, the threshold rate may be a minimum number of images of cytological objects of the specified classification that are displayed to the reviewer, or to a group of reviewers, within a specified amount of time, or within a specified number of cytological sample images.

The one or more processors may also receive input from the reviewer representing a reviewer classification of respective objects shown in the displayed images of said previously classified objects, and determine a percentage of said reviewer classifications that match respective previously determined classifications of said previously-classified objects.

Yet another embodiment directed to a computer-assisted method of classifying cytological samples includes using one or more processors to analyze images of cytological samples and identify cytological objects of interest within the sample images, wherein the one or more processors display images of the identified objects of interest to a reviewer, receive input from the reviewer representing a reviewer classification of the identified objects of interest shown in the displayed images, determine that a rate at which cytological objects of a specified classification (e.g., abnormal, pre-malignant, or malignant) are being displayed to the reviewer is below a threshold rate, and increase the rate at which cytological objects of the specified classification are being displayed by: accessing a database of images of previously-classified cytological objects, each of the objects in the database images having a previously-determined classification; and displaying to the reviewer, interspersed with the displayed images of the identified objects of interest from the samples, one or more images obtained from the database.

The one or more processors may also receive input from the reviewer representing a reviewer classification of the previously-classified cytological objects shown in the displayed images obtained from the database, and determine a percentage of reviewer classifications of displayed previously-classified objects that match the previously-determined classifications of the displayed previously-classified objects. The one or more processors may adjust the threshold rate based on the percentage of reviewer classifications of displayed previously-classified objects that match the previously-determined classifications of the displayed previously-classified objects.

Still another embodiment directed to a computer-assisted method of classifying cytological samples includes using one or more processors to analyze images of cytological samples and identify cytological objects of interest within the sample images, wherein the one or more processors display images of the identified objects of interest to a reviewer. Displaying images of the identified objects of interest to a reviewer may include displaying images of fields of view of respective cytological samples, each field of view image having one or more identified objects of interest therein.

In this embodiment, the one or more processors also access a database of images of previously-classified cytological objects, each of the objects in the database images having a previously-determined classification, and display to the reviewer, interspersed with the displayed images of the identified objects of interest from the samples, one or more images obtained from the database. The displayed one or more database images may be selected for display based on the objects in the database images having one or more characteristics similar to characteristics of the identified objects of interest from the samples, or based on the previously-classified objects having previously determined classifications similar to the reviewer classifications of the objects of interest from the samples.

In this embodiment, the one or more processors also receive input from the reviewer representing a reviewer classification of respective objects shown in the displayed images, determine a percentage of reviewer classifications of displayed previously-classified objects that match the previously-determined classifications of the displayed previously-classified objects, and based on the percentage, increase or decrease a frequency with which images obtained from the database are displayed relative to images of the identified objects of interest from the samples. For example, if the percentage of reviewer classifications of displayed previously-classified objects that match the previously-determined classifications of the displayed previously-classified objects is below a predetermined percentage, then the one or more processors may increase a frequency with which images obtained from the database are displayed relative to images of the identified objects of interest from the samples. Based on the percentage, the one or more processors may also determine a relative accuracy of the reviewer, or determine a confidence score of the reviewer classifications of the identified objects of interest from the samples. The one or more processors may also disregard the reviewer classifications of the identified objects of interest from the samples if the one or more processors determine that the percentage of reviewer classifications of displayed previously-classified objects that match the previously-determined classifications of the displayed previously-classified objects is below a predetermined percentage.

Yet another embodiment directed to a computer-assisted method of classifying biological samples includes using one or more processors to analyze images of biological samples, wherein the one or more processors display the analyzed biological sample images to a reviewer, access a database of previously-classified biological sample images, and display to the reviewer, interspersed with the displayed analyzed biological sample images, one or more of the previously-classified biological sample images obtained from the database. A number of the previously-classified biological sample images obtained from the database and displayed to the reviewer may be based upon a threshold rate at which biological sample images of a specified classification are to be displayed to the reviewer. The threshold rate may be a minimum number of biological sample images of the specified classification that are displayed to the reviewer, or to a group of reviewers, within a specified amount of time, or within a specified number of biological sample images. The specified classification may be the presence of one or more pre-malignant or malignant cytological objects in the biological sample image.

BRIEF DESCRIPTION OF THE DRAWINGS

Referring now to the drawings in which like reference numbers represent corresponding parts throughout and in which.

DETAILED DESCRIPTION OF ILLUSTRATED EMBODIMENTS

Figure 1:
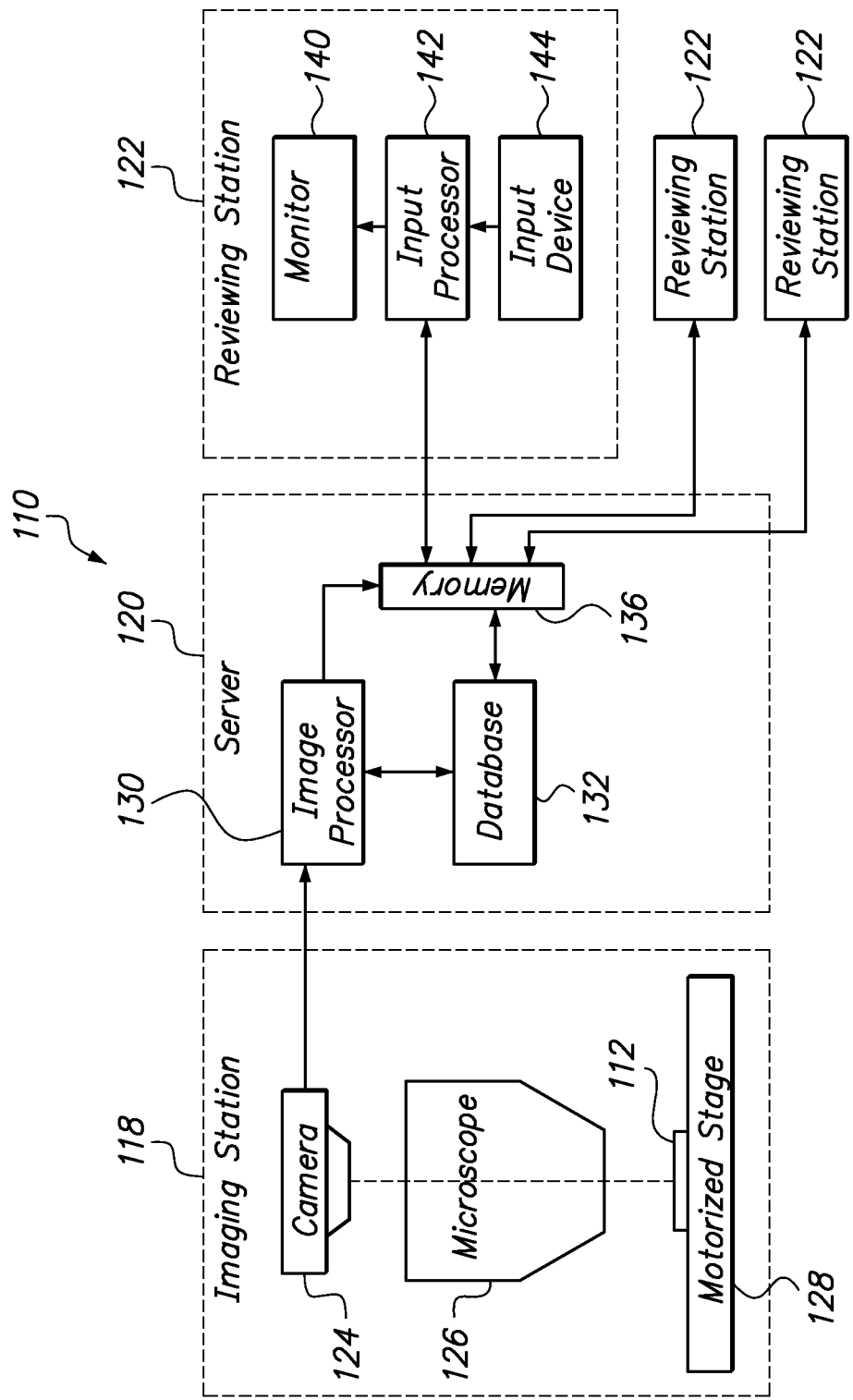
FIG. 1 is a block diagram of a system for assisting a reviewer with classifying biological specimen slides and automatically seeding images of previously-classified objects into the workflow of the reviewer.

Referring to FIG. 1, a biological screening system 110 constructed in accordance with the present invention is described. The system 110 is configured to process a series of microscope slides 112 in order to assist a reviewer, or cytotechnologist, in classifying a biological specimen 114 (shown in FIG. 2) disposed on the slide 112. The system 110 is further configured for automatically seeding images of previously-classified objects into the workflow of the reviewer such that the seeded images are indistinguishable from the specimen images.

With conventional classification systems and methods, it is difficult to measure the accuracy of slide classifications as a function of cytotechnologist because of the low prevalence of abnormal cells. Seeding digital images of previously-classified objects into the workflow of a cytotechnologist in accordance with the present invention is advantageous over conventional classification methods because such seeding facilitates accuracy quantification for quality control purposes, allows for viable accuracy measurement methods, and facilitates quality control monitoring. Measuring the accuracy of slide classifications as a function of cytotechnologist allows for continuous quality control monitoring of a complete lab's performance over time. Seeding images of previously-classified objects also has a performance-enhancing effect. Increasing the prevalence of targets (e.g., increasing the frequency with which images of abnormal cells appear in the workflow) increases attentiveness, thereby increasing the overall effective accuracy of cytotechnologists over time.

The system and method for seeding images of previously-classified objects into the workflow of cytological examinations in accordance with the present invention avoids a variety of difficulties associated with the conventional systems and methods of seeding pre-classified glass slides into the workflow. Such difficulties include degradation of the stain on glass slides, the inconvenience of physically shipping pre-classified glass slides between labs, problems associated with sharing glass slides among labs, and disguising glass slides in the workflow in order to prohibit cytotechnologists from identifying them as seeded slides. These difficulties are overcome with digital images in accordance with the present invention.

Although the system 110 can be used to assist in classifying any biological specimen, the system 110 lends itself particularly well to the presentation of cytological cervical or vaginal material, such as that typically found on a Pap smear slide. In this case, the cells in the specimen 114 may reflect abnormalities (e.g., cytolysis, atrophy, infection, damage), malignancy or premalignancy, such as Low Grade Squamous Intraepithelial Lesions (LSIL) or High Grade Squamous Intraepithelial Lesions (HSIL), as well as all other cytologic categories as defined by The Bethesda System for Reporting Cervical/Vaginal Cytologic Diagnosis. The biological specimen 114 will typically be placed on the slide 112 as a thin cytological layer. Preferably, a cover slip (not shown) is adhered to the specimen 114, thereby fixing the specimen 114 in position on the slide 112. The specimen 114 may be stained with any suitable stain, such as a Papanicolaou stain or a ThinPrep® Nuclear Stain.

Embodiments can also be used to characterize or classify other types of biological specimens including blood, urine, semen, milk, sputum, mucus, plueral fluid, pelvic fluid, synovial fluid, ascites fluid, body cavity washes, eye brushing, skin scrapings, a buccal swab, a vaginal swab, a pap smear, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, a microbial culture, a virus, samples of in vitro cell culture constituents, and other cytological and histological specimens. This specification refers to cytological cervical or vaginal specimens 114 (as on a Pap smear slide) to illustrate one manner in which embodiments can be implemented, and it should be understood that embodiments can be applied to various types of tissue and cells.

The system 110 generally comprises (1) an imaging station 118 for obtaining scanned images of the biological material 114 contained on the slide 112 and generating electronic image data from the images; (2) a server 120 for filtering the image data to identify the objects in the specimen 114 that are the most likely to be suspicious (e.g., abnormal, malignant, pre-malignant, etc.), otherwise referred to as objects of interest (OOIs); and (3) a plurality of reviewing stations 122 (3 shown), each of which presents images of the objects to the cytotechnologist.

Although the system 110 is described as being used to assist in classifying individual objects and to seed images of individual objects into the workflow of a reviewer, it should be appreciated that the system 110 may additionally or alternatively be used to assist in classifying and seeding images of fields of view (FOVs) rather than of individual objects. Thus, the server 120 may be configured for identifying FOVs in the specimen 114 that are the most likely to contain OOIs or clusters of OOIs, otherwise referred to as fields of interest (FOIs).

The imaging station 118 comprises a camera 124, microscope 126, and motorized stage 128 which supports the slide 112. The slide 112 is mounted on the motorized stage 128, which moves the slide 112 relative to the viewing region of the microscope 126, while the camera 124 captures magnified images of the slide 112 through the microscope 126. The camera 124 may be any one of a variety of conventional cameras, such as a charge coupled device (CCD) camera, which alone or in conjunction with other components, such as an analog-to-digital (ND) converter, can produce a digital output of sufficient resolution to allow processing of the captured images. The shutter speed of the camera 124 is preferably relatively high, so that the scanning speed and/or number of images taken can be maximized.

The server 120 comprises (1) an image processor 130 that is configured to identify the OOIs (or FOIs) from the image data acquired from the camera 124; (2) a database 132 of images of previously-classified cytological objects (or previously classified FOVs); and (3) a memory or storage device 136 configured for storing the images of the identified OOIs (or FOIs). It should be appreciated that the components of the server 120 could be arranged differently. For example, functions performed by the processor 130 can be performed by a single processor, or alternatively, performed by more than one processor. Further, the memory 136 can be divided into several memories. In another example, the memory 136 may be a part of the image processor 130 or a separate component.

Individual images of previously-classified objects are manually selected by cytotechnologists and stored in the predefined database 132. This database 132 of images of preselected and categorized objects is used for seeding pre-classified digital images of objects into the workflow of cytotechnologist slide classification. Each of the objects in the images in the database 132 has a previously-determined classification associated therewith. For example, the objects in the images in the database 132 may be previously classified as "abnormal," "malignant," "pre-malignant," "HSIL," "LSIL," "carcinoma in situ," or the like. As discussed in more detail below, the reviewer is unaware that previously classified objects are appearing in the workflow. Thus, a reviewer may associate a reviewer-determined classification with an object that already has a previously-determined classification. This reviewer-determined classification is compared to the previously-determined classification for that object for quality control purposes, examples of which are discussed in more detail below.

Although the database 132 is described as containing images of cytological objects, it should be well understood that the database 132 may alternatively or additionally include previously-classified biological sample images. As discussed above, the present invention is not limited to cytological specimens. Embodiments can also be used to characterize or classify other types of biological specimens, and therefore, in these embodiments, the database 132 may contain previously-classified images of other types of biological specimens.

It should also be well understood that the database 132 may contain images of fields of view, rather than images of individual objects. The images of the fields of view in the database 132 may each contain at least one previously-classified object. Put another way, the images in the database 132 may be of previously-classified fields of view.

Referring still to FIG. 1, a total of three reviewing stations 122 are shown coupled to the server 120, so that up to three cytotechnologists have simultaneous access to the pertinent information stored in the server 120. Each reviewing station 122 comprises (1) a monitor 140 for displaying images of objects (or FOVs) for the cytotechnologist to review; (2) an input processor 142 coupled to the monitor 140; and (3) a user input device 144 coupled to the input processor 142. The monitor 140 is configured for displaying images of the identified OOIs (or identified FOIs) from the specimen 114 as well as images obtained from the database 132. The images may be displayed one at a time or several images may be displayed simultaneously in an array. In order to allow the reviewer to advance from one image to the next image, or from one array to the next array, the input device 144 may include an activation switch (not shown). In this sense, the reviewing station 122 is semi-automatic. Alternatively, the individual images or arrays are automatically advanced from one to the next. In this case, the processor 142 may optionally pause at each image or each array for a predetermined amount of time. In this sense, the reviewing station 122 is fully automatic.

As the images of the identified OOIs and the images from the database 132 are presented on the monitor 140, the cytotechnologist reviews the displayed images and makes decisions about the level of abnormality of the objects in the displayed images. With the user input device 144, the cytotechnologist is able to input information regarding the classification of the object in the displayed image, including classification decisions and/or the perceived level of dysplasia or carcinoma. For example, the input device 144 may be configured to receive input such as "abnormal," "malignant," "pre-malignant," "HSIL," "LSIL," "carcinoma in situ," or the like. The user input device 144 may include a keyboard, a mouse, a joystick, a touch screen, or the like.

Further aspects of suitable components of the system 110 are described in U.S. Patent Application Publication No. 2004/0253616 A1, the contents of which are hereby incorporated herein by reference.

Figure 3:
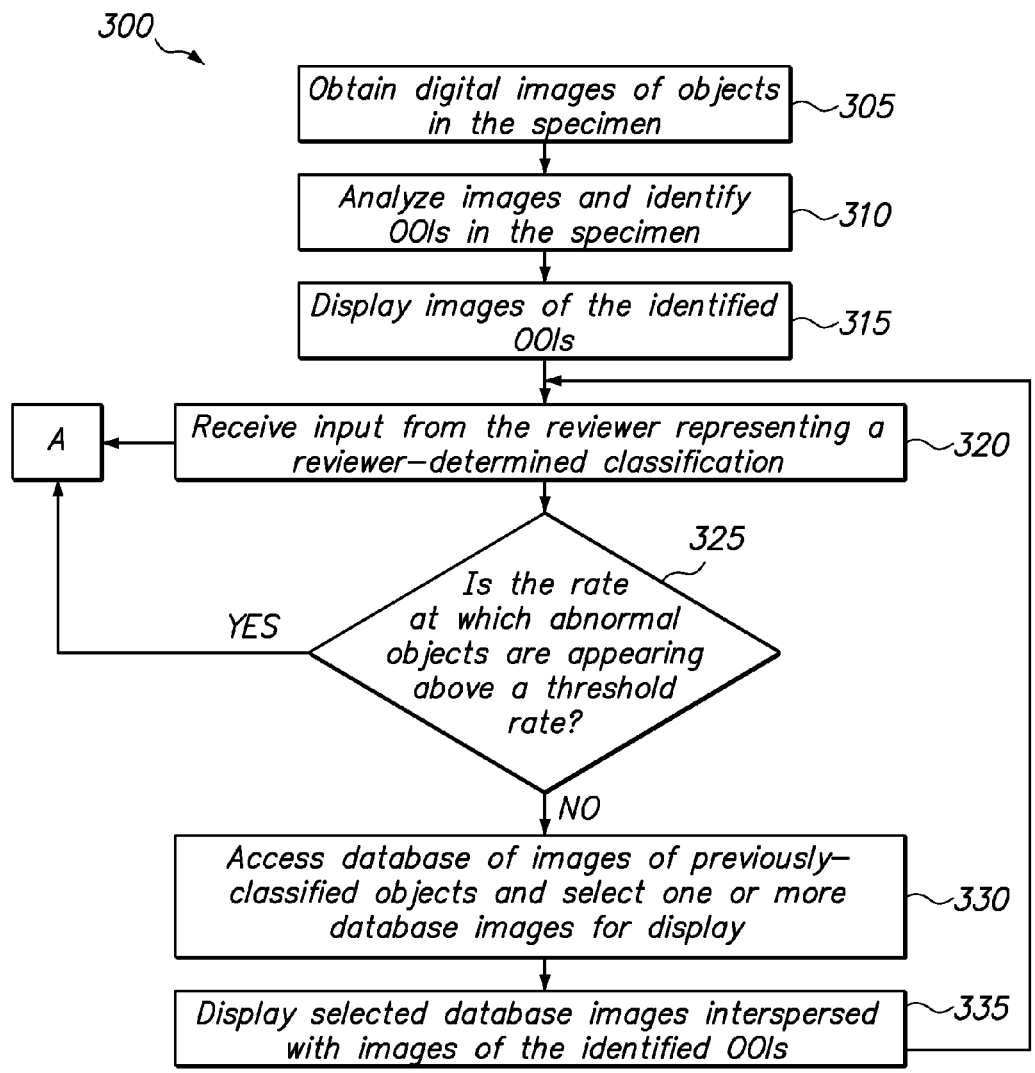
FIG. 3 is a flow chart of a computer-assisted method of classifying biological specimens and automatically seeding images of previously-classified objects into the workflow of the reviewer.

With reference to FIG. 3, a computer-assisted method 300 of classifying cytological samples and seeding images of previously-classified objects into the classification workflow using the system 110 shown in FIG. 1 is described. The method 300 depicts an embodiment where a reviewer or a lab reviews a minimum number of images of objects of a specified classification (or biological sample images of a specified classification) within a pre-determined amount of time. In other words, there is a "threshold rate" at which images of objects of the specified classification are displayed to the reviewer or to the lab. The images of the objects of the specified classification may be images of abnormal objects, malignant objects, pre-malignant objects, and/or the like.

As discussed in more detail below, images from the database 132 may be added to the workflow of the individual reviewer, or of the lab as a whole, in order to achieve the threshold rate. The actual rate at which images of objects of the specified classification are displayed to the reviewer is continuously monitored and compared to the threshold rate. If the actual rate at which images of objects of the specified classification are displayed to the reviewer falls below the threshold rate, then images from the database 132 are inserted into the workflow in order to increase the prevalence of images of objects of the specified classification and to achieve the threshold rate. The reviewer's alertness is increased by increasing the prevalence of images of objects of the specified classification in the reviewer's workflow. In addition, increasing the prevalence of images of objects of the specified classification in the reviewer's workflow increases the amount of data that may be used in quality control evaluations.

The threshold rate may be defined as a minimum number of images of objects of a particular classification that are displayed to the reviewer within a specified amount of time, such as an hour, a day, a week, a month, etc. For example, the threshold rate may be 100 images of HSIL objects and 100 images of LSIL objects displayed to the reviewer within a week. If the reviewer is classifying identified OOIs from the sample images at a rate of 65 HSIL objects per week and 75 LSIL objects per week, then the processor 142 determines that the rate at which images of HSIL and LSIL objects are appearing in the reviewer's workflow is below the threshold rate of 100 images of HSIL objects and 100 images of LSIL objects per week. In this example, 35 images of HSIL objects and 25 images of LSIL objects need to be added to the reviewer's workflow in order to achieve the threshold rate. Thus, the processor 142 selects 35 images from the database 132 having "HSIL" classifications associated therewith and 25 images from the database having "LSIL" classifications associated therewith, and inserts those images into the workflow of the reviewer. Thus, during the week, the images displayed to the reviewer include 65 images of HSIL objects from the specimen and 35 images of HSIL objects from the database 132, for a total of 100 images of HSIL objects reviewed during the week. The images displayed to the reviewer also include 75 images of LSIL objects from the specimen and 25 images of LSIL objects from the database 132, for a total of 100 images of LSIL objects reviewed during the week. "HSIL objects from the specimen" refers to identified OOIs from the specimen that the reviewer classifies as "HSIL." Similarly, "LSIL objects from the specimen" refers to identified OOIs from the specimen that the reviewer classifies as "LSIL."

The threshold rate may be based on a reviewer's accuracy. That is, a reviewer with high accuracy may have a smaller threshold rate than a reviewer with low accuracy. In this manner, it is anticipated that the accuracy of the low-accuracy reviewer would be increased due to increased prevalence of targets. In addition, the accuracy of the low-accuracy reviewer could be monitored more closely and efficiently by increasing the prevalence of targets. As discussed in more detail below, the reviewer's accuracy may be evaluated based on the number, or percentage, of previously classified objects that the reviewer classifies correctly.

Rather than being based upon a specified time period, the threshold rate may be defined on a per-slide, or per-image, basis. That is, the threshold rate may be defined as a minimum number of images of objects of a specified classification that are displayed to the reviewer during the review of a specified number of slides, or a specified number of sample images. For example, the threshold rate may be 100 images of abnormal objects displayed to the reviewer for every 20 slides reviewed, or for every 400 sample images reviewed.

Further, the threshold rate may be applied to a lab as a whole, rather than to each individual reviewer in a lab. That is, the collective rate at which images of objects of a specified classification are displayed to all of the reviewers that work in a lab would be at or above the threshold rate. For example, the threshold rate for all of the reviewers in a lab as a whole may be 500 images of HSIL objects and 500 images of LSIL objects within a week, 100 images of abnormal objects per day, 200 images of abnormal objects per 2000 sample images, or another such pre-determined rate.

Figure 2:
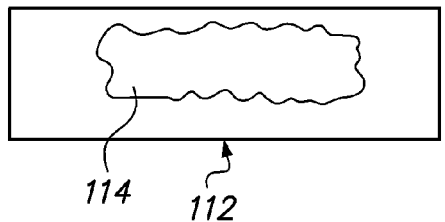
FIG. 2 is a plan view of a biological specimen slide.

The steps in the method 300 will now be described with reference to FIGS. 1-3. First, the camera 124 obtains digital images of objects (or FOVs) in the biological specimens 114 at step 305. More particularly, the slide 112 carrying a cytological specimen 114 is mounted on the motorized stage 128, which moves or scans the slide 112 relative to the viewing region of the microscope 126, while the camera 124 captures images over the entire biological specimen 114 or portions thereof. Each pixel of each image acquired by the camera 124 can be converted into an eight-bit value (0 to 255) depending on its optical transmittance, with "00000000" being the assigned value for least amount of light passing through the pixel, and "11111111" being the assigned value for a greatest amount of light passing through the pixel.

At step 310, the images or image data acquired by the camera 124 are provided to the image processor 130, which analyzes the images or image data in order to identify OOIs (or FOIs) in the specimen 114. For example, the image processor 130 may perform primary and secondary segmentation as described in U.S. Patent Application Publication No. 2004/0253616, the contents of which were previously incorporated herein by reference, and measure, determine or extract various features for each of the individual objects and clustered objects in the specimen 114. The image processor 130 may then calculate an object score for each object based on the measured values of these features. Based on this score, the image processor 130 can identify or select objects and clustered objects that are considered OOIs. The images of the identified OOIs may then be stored in memory 136 for future reference.

At step 315, the images of the identified OOIs are then provided to the input processor 142 and displayed on the monitor 140 of the review station 122. As discussed above, the identified OOIs may be displayed one at a time, or may be displayed in an array. Alternatively or additionally, images of fields of view of the specimen 114 are displayed to the reviewer, and each field of view image has one or more identified OOIs therein.

In one embodiment, the identified OOIs may be displayed in order. For example, the identified OOIs that are determined to be the most likely to be suspicious are displayed first. In one embodiment, where the image processor 130 calculates a score for each object, the OOIs are displayed in order depending on their scores. For example, the OOI with the highest score is displayed first and then the remaining OOIs are displayed in order of descending score. In another embodiment, OOIs having similar characteristics are displayed simultaneously in an array. In this embodiment, the processor 130 may be configured to evaluate certain characteristics of the OOIs and then group OOIs having similar characteristics together in an array. For example, objects having similar cell sizes, similar nucleus to cytoplasm area ratios, similar nuclear corrected integrated optical densities, or similar cytoplasmic vacuolization may be grouped together.

While the images of the OOIs are being displayed, the reviewer is able to input information related to the displayed images, such as reviewer-determined classifications of the objects (or FOVs) shown in the displayed images. For example, if a cytotechnologist viewing the images on the monitor 140 determines that one of the OOIs (or FOIs) in the displayed images appears to be abnormal, the cytotechnologist may input a reviewer-determined classification of "abnormal" using the input device 144. The input processor 142 receives this reviewer-determined classification at step 320.

After the input is received at step 320, the input may be analyzed, as discussed in more detail below with reference to FIGS. 5-8. In addition, after the input is received at step 320, the processor 142 determines, in step 325, whether the rate at which images of objects of a specified classification (or biological sample images of a specified classification) are appearing in the workflow is above a threshold rate. If the rate is above the threshold rate, then it is unnecessary to add images from the database 132 to the workflow, and the method proceeds to the input analysis steps, which are discussed in more detail below with reference to FIGS. 5-8. However, if the rate is below the threshold rate, then the processor 142 determines that images from the database 132 need to be added to the reviewer's workflow in order to increase the rate at which images of objects of a specified classification are appearing in the workflow in order to achieve the threshold rate.

Thus, in step 330, the image processor 130 and/or the input processor 142 accesses the database 132 of images of previously-classified cytological objects and selects for display one or more of the images from the database 132. The image processor 130 and/or the input processor 142 performs step 330 automatically, without being prompted by the reviewer. Thus, the reviewer is unaware that the database 132 is being accessed or that images are being selected from the database 132.

The images from the database 132 are selected based upon which particular classification needs to be displayed to the reviewer in order to reach the threshold rate for that particular classification. For example, if the system determines at step 325 that the rate at which images of LSIL objects are appearing in the workflow is below the threshold rate for the "LSIL" classification, then an image of an object having a previously-determined classification of "LSIL" is selected from the database 132 at step 330. Similarly, if the system determines at step 325 that the rate at which images of HSIL objects are appearing in the workflow is below the threshold rate for the "HSIL" classification, then an image of an object having a previously-determined classification of "HSIL" is selected from the database 132 at step 330.

In step 335, the one or more selected database images are displayed on the monitor 140 interspersed with the displayed images of the identified OOIs from the specimens 114. For example, if the images of the identified OOIs are being displayed one at a time, one of the selected database images is inserted in the workflow. If the images of the identified OOIs are being displayed in an array, one of the selected database images may be one of the images in the array. The reviewer's alertness is increased by displaying the selected database images interspersed with the displayed images of the identified OOIs from the specimens 114. The image processor 130 and/or the input processor 142 performs step 335 automatically, without being prompted by the reviewer. Thus, the reviewer is unaware that images from the database 132 are being displayed within the reviewer's workflow.

Steps 320, 325, 330, and 335 are repeated until the threshold rate is reached. Further, steps 320, 325, 330, and 335 may be occurring simultaneously with the input analysis steps discussed below with reference to FIGS. 5-8. That is, the input received in step 320 may be continuously analyzed while images from the specimen 114 and the database 132 are being displayed.

It should be well understood that each of the steps 310, 315, 320, 325, 330, and 335 depicted in FIG. 3 may be performed by the image processor 130 and/or the input processor 142. Although some of these steps are described as being performed by either the image processor 130 or the input processor 142, it should be well understood that the steps are described in this manner for exemplary purposes only, and that either the image processor 130 or the input processor 142 is capable of performing each of these steps. Further, the system 110 may include one or more additional processors for performing these steps.

In the method depicted in FIG. 3, the criteria for selecting images from the database 132 is based upon a threshold rate. Images of objects having a particular classification are chosen from the database 132 and displayed to the reviewer until the reviewer has reviewed a minimum number of images of objects having that particular classification within a specified amount of time. Alternatively or additionally, the images from the database 132 may be selected for display based upon reviewer input regarding the OOIs from the specimen 114, based upon characteristics of the OOIs from the specimen 114, and/or may be selected randomly. These selection criteria are discussed in more detail below with reference to FIG. 4.

Figure 4:
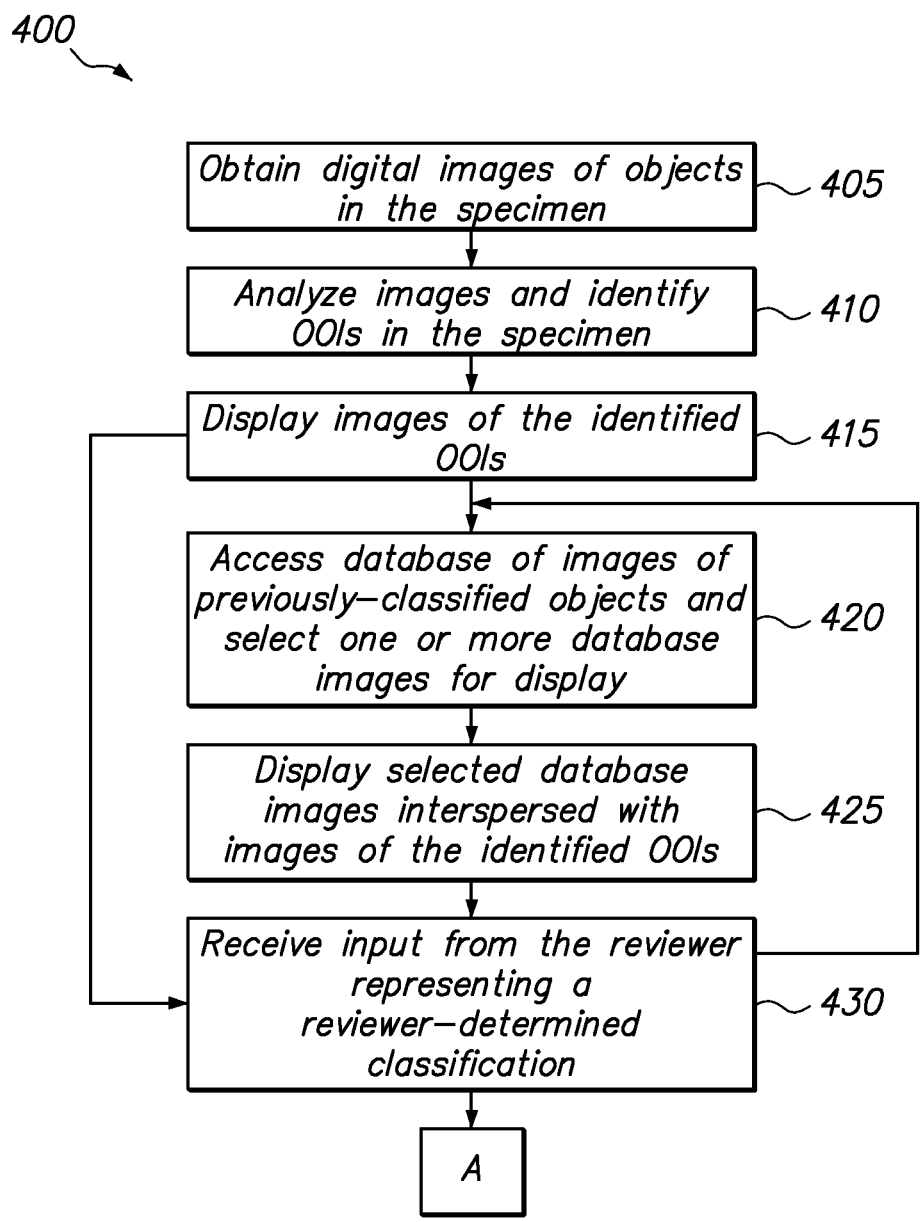
FIG. 4 is a flow chart of another embodiment of a computer-assisted method of classifying biological specimens and automatically seeding images of previously-classified objects into the workflow of the reviewer.

FIG. 4 depicts a computer-assisted method 400 of classifying cytological samples and seeding images of previously-classified objects into the classification workflow using the system 110 shown in FIG. 1. The method 400 is similar to the method 300 described above, except that the step of determining whether the threshold rate has been reached is omitted in the method 400. However, it should be well-understood that the method 400 may include a step of determining whether the threshold rate has been reached. That is, a step of determining whether the threshold rate has been reached is not excluded from the method 400. Alternatively, the method 400 may continuously or intermittently seed images from the database 132 into the workflow without regard to a threshold rate at which images of objects of a specified classification are displayed.

With reference to FIG. 4, the method 400 will now be described. First, digital images of objects in the biological specimens 114 are obtained in step 405. Next, the images of the objects are analyzed in order to identify OOIs in the specimen 114 at step 410. At step 415, images of the identified OOIs are displayed on the monitor 140 for review by a cytotechnologist. Steps 405, 410 and 415 are substantially similar to steps 305, 310, and 315, respectively, which are described in greater detail above with reference to FIG. 3.

After images of the identified OOIs are displayed in step 415, the reviewer is able to input data regarding the displayed OOIs, such as reviewer-determined classifications of the displayed OOIs. This input is received at step 430. While the processor 142 is receiving input, the processor 142 is simultaneously seeding images from the database 132 into the workflow by performing steps 420 and 425.

At step 420, the image processor 130 and/or the input processor 142 accesses the database 132 of images of previously-classified cytological objects and selects for display one or more of the images from the database 132. The image processor 130 and/or the input processor 142 performs step 420 automatically, without being prompted by the reviewer. Thus, the reviewer is unaware that the database 132 is being accessed or that images are being selected from the database 132.

In one embodiment, the criteria for selecting the images from the database 132 is based upon input received from the reviewer at step 430. Based on this input, the input processor 142 is programmed to select images from the database 132 where the objects in the selected database images have previously-determined classifications that are the same as, or at least similar to, the reviewer-determined classifications of the identified OOIs that are received at step 430. For example, if the reviewer input for images corresponding to a particular slide includes several "LSIL" classifications, the processor 103 and/or 142 would select images from the database 132 of objects that were previously classified as "LSIL." These selected images would be seeded in the workflow of the reviewer. In this manner, the database images are seamlessly inserted into the workflow because the specimen being reviewed has already been determined to include LSIL objects, and thus, the reviewer will not be surprised to see LSIL objects appear in the workflow.

In addition, or alternatively, the criteria for selecting images from the database 132 may be based upon the analysis of the OOIs in the samples 114. This analysis is performed in step 410 and described in more detail above with reference to step 310 in FIG. 3. Based on this analysis, the image processor 130 selects images from the database 132 of objects that have characteristics similar to the characteristics of the identified OOIs from the samples 114. For example, in step 410, the image processor 130 may analyze the cell sizes of the OOIs in the specimen 114, and then, in step 420, may select from the database 132 images of objects having cell sizes that are similar to the cell sizes of the identified OOIs in the specimen 114.

Next, in step 425, the one or more selected database images are displayed on the monitor 140 interspersed with the displayed images of the identified OOIs from the specimens 114, thereby increasing the reviewer's alertness. If the images of the identified OOIs are being displayed one at a time, one of the selected database images is inserted in the workflow. If the images of the identified OOIs are being displayed in an array, one of the selected database images may be one of the images in the array. The image processor 130 and/or the input processor 142 performs step 425 automatically, without being prompted by the reviewer. Thus, the reviewer is unaware that images from the database 132 are being displayed within the reviewer's workflow.

Because the database images have been carefully selected to be similar to the images of the OOIs, the database images should be indistinguishable from the images of the OOIs from the specimen 114. Thus, the selected database images of the previously-classified objects are well-disguised among the images of the OOIs, and the reviewer is unaware of being assessed or monitored. It should be appreciated that steps 415, 420, 425, and 430 may occur in any order, or may be occurring simultaneously. Steps 420 and 425 may be repeated continuously during review of a specimen, intermittently during review of a specimen, until a desired number of images from the database have been seeded into the workflow, or until a threshold rate of images of objects of a specified classification appearing in the workflow has been reached.

In step 430, the reviewer inputs data regarding the displayed images. For example, the input processor 142 may receive input from the reviewer representing reviewer classifications of the objects in the displayed images. Because the reviewer is unaware of which of the displayed images have been previously classified (e.g., which of the displayed images are obtained from the database 132), the reviewer classification may be associated with the identified OOIs from the samples 114 or with the previously-classified objects. After input is received from the reviewer in steps 320 and/or 430, the input may be analyzed as discussed in more detail with reference to FIGS. 5-8 below.

It should be well understood that each of the steps 410, 415, 420, 425, and 430 depicted in FIG. 4 may be performed by the image processor 130 and/or the input processor 142. Although some of these steps are described as being performed by either the image processor 130 or the input processor 142, it should be well understood that the steps are described in this manner for exemplary purposes only, and that either the image processor 130 or the input processor 142 is capable of performing each of these steps. Further, the system 110 may include one or more additional processors for performing these steps.

When the reviewer determines that a displayed object is abnormal, the reviewer inputs an "abnormal" classification for that object at step 320 or 430. This input is referred to as the "reviewer-determined classification." If that displayed object is obtained from the database 132, then, unbeknownst to the reviewer, the displayed object already has a previously-determined classification associated with it. In this situation, the reviewer-determined classification may be compared to the previously-determined classification of that object in order to determine whether the reviewer-determined classification matches the previously-determined classification. If that displayed object is one of the OOIs from the specimen 114, then the reviewer-determined classification is the only classification associated with that object and the comparison is not performed. If the reviewer determines that a displayed object is normal, the reviewer may not provide any input to the input processor 142. However, if that object that the reviewer has determined is normal is actually a previously-classified object from the database 132, then the input processor 142 determines that the reviewer-determined classification does not match the previously-determined classification for that object.

Figure 5:
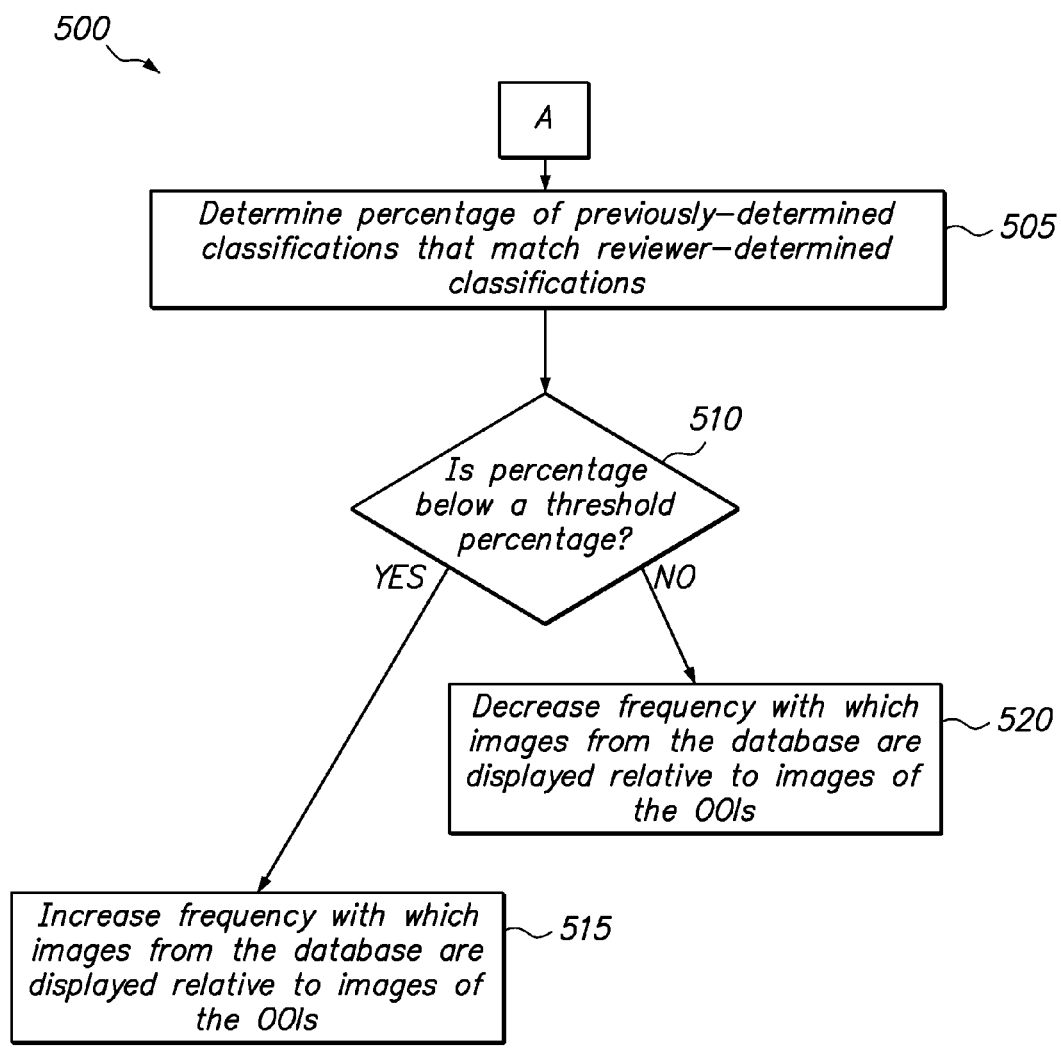
FIG. 5 is a flow chart of a method for analyzing reviewer input.

With reference now to FIG. 5, an input analysis method 500 begins at step 505 by determining the percentage of previously-determined classifications that match reviewer-determined classifications. This percentage is determined by first comparing a reviewer-determined classification of a previously-classified object to the previously-determined classification of that object. Based on this comparison, the input processor 142 determines whether the reviewer-determined classification matches the previously-determined classification for that particular object. The input processor 142 may then determine a percentage of reviewer-determined classifications that match the previously-determined classifications for the displayed previously-classified objects. If there is no reviewer input associated with a previously-classified object, then the input processor 142 determines that the respective classifications for that object do not match.

Next, in step 510, the processor 142 determines whether the percentage calculated in step 505 is below a threshold percentage. If the percentage of reviewer classifications that match the previously-determined classifications is high (i.e., above a predetermined threshold), the frequency with which images obtained from the database 132 are displayed to the reviewer may be decreased in step 520. The frequency may be decreased because a high percentage indicates that the reviewer's assessments are accurate and that the reviewer is attentive and does not require high target prevalence. Conversely, if the percentage of reviewer classifications that match the previously-determined classifications is low (i.e., below the predetermined threshold), then the frequency with which images obtained from the database 132 are displayed to the reviewer may be increased in step 515. The increased frequency may increase the reviewer's attentiveness and may provide more data with which to assess the accuracy of the reviewer. Similarly, the threshold rate at which images of objects of a specified classification are displayed to the reviewer may be adjusted based on the percentage calculated in step 505. If the percentage calculated in step 505 is high, then the threshold rate may be decreased. Conversely, if the percentage calculated in step 505 is low, then the threshold rate may be increased.

Figure 6:
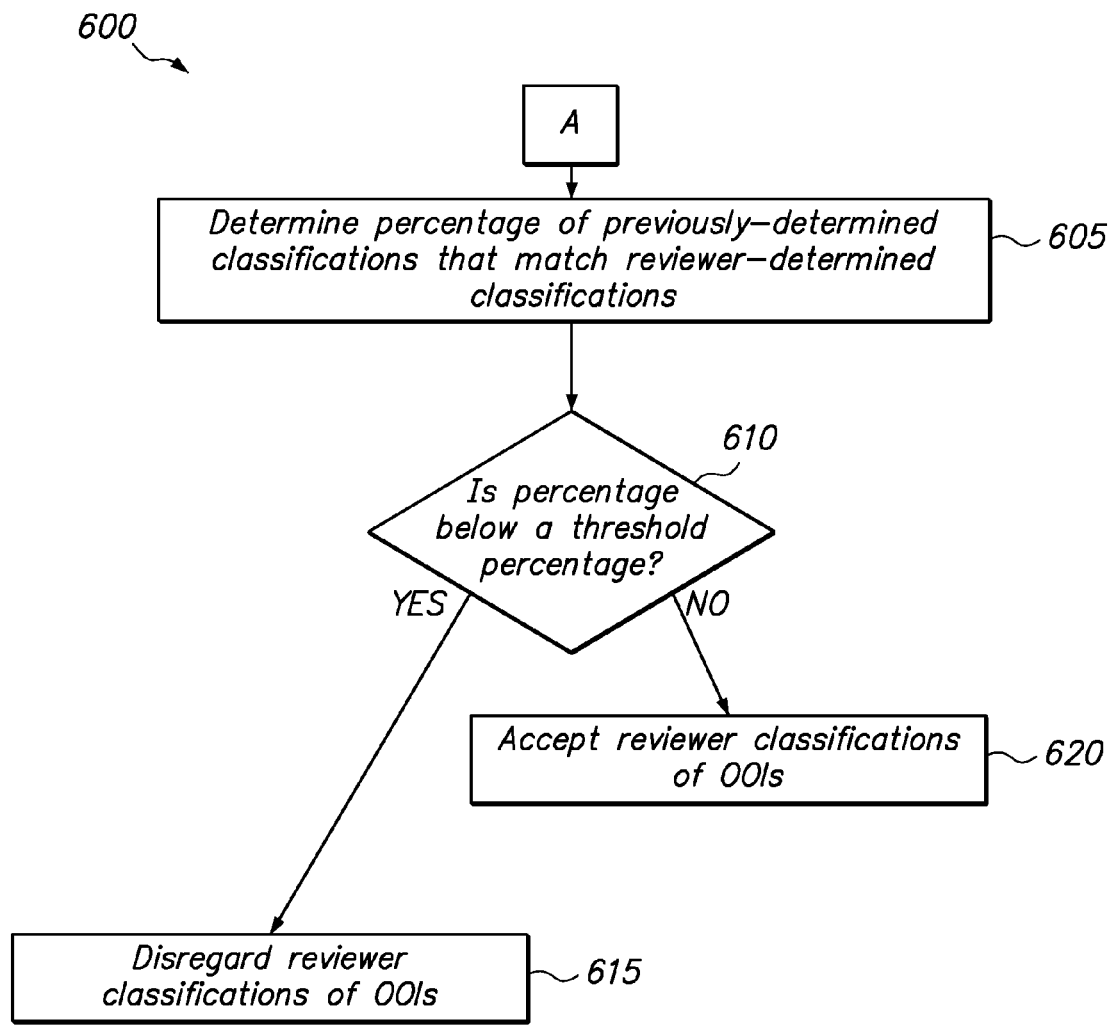
FIG. 6 is a flow chart of another embodiment of a method for analyzing reviewer input.

Another method 600 of analyzing the reviewer input is depicted in FIG. 6. In this method 600, the percentage of previously-determined classifications that match reviewer-determined classifications is determined in step 605. This step is substantially the same as step 505, which is described in greater detail above with reference to FIG. 5. Next, at step 610, the processor 142 determines whether the percentage calculated in step 605 is below a threshold percentage. If the percentage determined in step 605 is below the threshold percentage, then it may be assumed that the reviewer's accuracy in classifying the OOIs from the specimen 114 is low. Thus, in step 615 the reviewer classifications of the identified OOIs from the samples 114 may be disregarded if the percentage is below the threshold percentage. If the percentage determined in step 605 is not below the threshold, then it may be assumed at the reviewer's accuracy in classifying the OOIs from the specimen 114 is high. Thus, in step 620, the reviewer classifications of the identified OOIs from the specimens 114 may be accepted if the percentage is above the threshold percentage.

Figure 7:
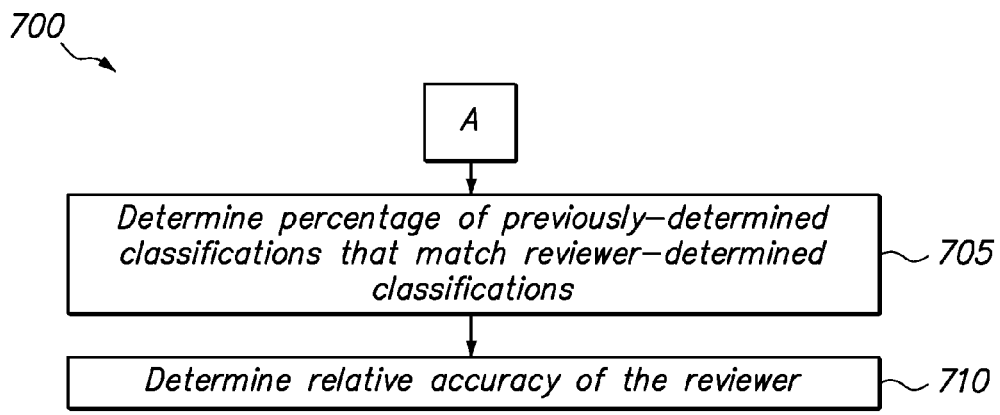
FIG. 7 is a flow chart of yet another embodiment of a method for analyzing reviewer input.

Another method 700 of analyzing the reviewer input is depicted in FIG. 7. In this method 700, the percentage of previously-determined classifications that match reviewer-determined classifications is determined in step 705. This step is substantially the same as step 505, which is described in greater detail above with reference to FIG. 5. Next, at step 710, a relative accuracy of the reviewer may be determined based on the percentage determined in step 705. If the percentage is high, the accuracy of the reviewer is high. If the percentage is low, the accuracy of the reviewer is low. If the accuracy of the reviewer is low, the reviewer may require more practice or more training. For example, if the accuracy of the reviewer is low, the threshold rate at which images of objects of a specified classification are displayed to the reviewer may be increased.

Figure 8:
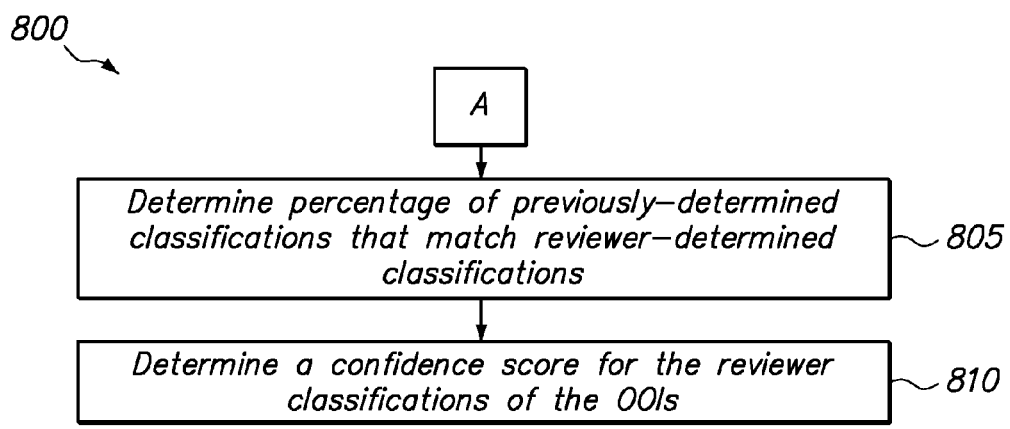
FIG. 8 is a flow chart of still another embodiment of a method for analyzing reviewer input.

Another method 800 of analyzing the reviewer input is depicted in FIG. 8. In this method 800, the percentage of previously-determined classifications that match reviewer-determined classifications is determined in step 805. This step is substantially the same as step 505, which is described in greater detail above with reference to FIG. 5. Next, at step 810, a confidence score of the reviewer classifications of the identified OOIs from the samples 114 may be determined based on the percentage calculated in step 805. For example, if the percentage calculated in step 805 is high, then it can be assumed that the reviewer's accuracy with classifying the OOIs is also high. As such, the confidence score determined in step 810 may be high. If the percentage is low, then it can be assumed that the reviewer's accuracy with classifying the OOIs is also low. As such, the confidence score determined in step 810 may be low.

It should be well understood that each of the steps depicted in FIGS. 5-8 may be performed by the image processor 130 and/or the input processor 142. Although some of these steps are described as being performed by either the image processor 130 or the input processor 142, it should be well understood that the steps are described in this manner for exemplary purposes only, and that either the image processor 130 or the input processor 142 is capable of performing each of these steps. Further, the system 110 may include one or more additional processors for performing these steps.

Although particular embodiments have been shown and described, it should be understood that the above discussion is not intended to limit the scope of these embodiments. Various changes and modifications may be made without departing from the scope of the claims.

Additionally, embodiments can be utilized to process and analyze various types of specimens other than cytological cervical or vaginal specimens, which are provided as examples of how embodiments may be implemented. Moreover, embodiments can involve specimens held or carried by various specimen carriers including slides and vials. Further, it should be understood that embodiments can be applied for classification of different types of specimens and may be used for other purposes.

Further, embodiments can be embodied as a computer program product for use with a biological specimen classification system and that embodies all or part of the functionality previously described herein. Such an implementation may comprise a series of computer readable instructions either fixed on a tangible medium, such as a computer readable medium, for example, diskette, CD-ROM, ROM, or hard disk, or transmittable to a computer system, via a modem or other interface device.

Thus, embodiments are intended to cover alternatives, modifications, and equivalents that fall within the scope of the claims.

What is claimed is:

1. A computer-assisted method of classifying cytological samples, comprising:
    using one or more processors to
        display previously unclassified cytological sample images to a reviewer,
        receive classifications of the displayed cytological sample images from the reviewer,
        monitor a reviewer classification rate equal to a number of displayed previously unclassified cytological sample images receiving a specified classification by the reviewer divided by a total number of previously unclassified cytological sample images displayed to the reviewer, and
    if the monitored reviewer classification rate is below a threshold rate, display to the reviewer, interspersed with the displayed previously unclassified cytological sample images, one or more images of the specified classification obtained from a database of images of previously classified cytological samples.

2. The method of claim 1, wherein the specified classification indicates that the image includes abnormal cytological objects.

3. The method of claim 1, wherein the one or more processors
    receive reviewer determined classifications of the displayed images obtained from the database of images of previously classified cytological samples; and
    determine a percentage of said reviewer determined classifications that indicate said displayed images are of the specified classification.

4. The method of claim 1, wherein displaying the previously unclassified cytological sample images to a reviewer comprises displaying images of fields of view of respective cytological samples, each field of view image having one or more previously identified objects of interest therein.

* * * * *